US009884083B2

(12) United States Patent
Tawashi et al.

(10) Patent No.: US 9,884,083 B2
(45) Date of Patent: *Feb. 6, 2018

(54) PALM POLLEN FOR TREATMENT OF MUCOSITIS AND INFLAMMATORY CONDITIONS

(71) Applicant: ClinAvenir, LLC, Los Altos, CA (US)

(72) Inventors: Rashad Tawashi, Beaconsfield (CA); Mona Tawashi, Los Altos, CA (US)

(73) Assignee: ClinAvenir, LLC, Los Altos, CA (US)

( * ) Notice: Subject to any disclaimer, the term of this patent is extended or adjusted under 35 U.S.C. 154(b) by 698 days.

This patent is subject to a terminal disclaimer.

(21) Appl. No.: 14/298,971

(22) Filed: Jun. 9, 2014

(65) Prior Publication Data
US 2015/0352170 A1 Dec. 10, 2015

Related U.S. Application Data

(60) Provisional application No. 61/834,805, filed on Jun. 13, 2013.

(51) Int. Cl.
A61K 36/889 (2006.01)

(52) U.S. Cl.
CPC .................. A61K 36/889 (2013.01)

(58) Field of Classification Search
CPC .................................................... A61K 36/889
See application file for complete search history.

(56) References Cited

U.S. PATENT DOCUMENTS

| | | | |
|---|---|---|---|
| 4,528,267 A | 7/1985 | Calenoff et al. | |
| 4,716,120 A | 12/1987 | Tsay et al. | |
| 4,751,791 A | 6/1988 | Al-Rawi | |
| 5,013,552 A | 5/1991 | Amer et al. | |
| 5,275,819 A | 1/1994 | Amer et al. | |
| 6,790,464 B2 | 9/2004 | Kuok et al. | |
| 7,883,726 B2 | 2/2011 | Crutchfield, III | |
| 9,060,924 B2* | 6/2015 | Tawashi | A61K 36/889 |
| 2002/0121046 A1 | 9/2002 | Yamashita | |
| 2005/0048020 A1 | 3/2005 | Willie | |
| 2005/0063994 A1 | 3/2005 | Caplan et al. | |
| 2009/0214628 A1 | 8/2009 | De Rijk | |
| 2010/0138951 A1 | 6/2010 | Nelson et al. | |
| 2013/0011349 A1* | 1/2013 | Tawashi | A61K 36/889 424/59 |

FOREIGN PATENT DOCUMENTS

| | | |
|---|---|---|
| WO | WO 92/19229 | 11/1992 |
| WO | WO 98/50005 | 11/1998 |

OTHER PUBLICATIONS

Mohamed et al. International J. Andrology. Jun. 2005. vol. 28, Suppl. 1, p. 103, Poster No. P-151.*
Elberry et al. J. Inflammation. 2011. vol. 8, pp. 1-13.*
Barzin et al. Advances in Environmental Biol. 2011. vol. 5, No. 12, pp. 3716-3718.*
Hassan, Hazem M.M., Chemical Composition and Nutritional Value of Palm Pollen Grains, 2011, Global J. Biotech & Biochem, 6(1): 01-07.
Bahmanpour S., et al., Effect of Phoenix Dactylifera Pollen on Sperm Parameters and Reproductive System of Adult Male Rats, Iran J. Med Sci., Dec. 2006; vol. 31, No. 4: 208-212.
Bennett, R.D., et al., Isolation of Estrone and Cholesterol from the Date Palm, Phoenix Dactylifera L., Phytochemistry, Mar. 1966; 5(2): 231-235.
El Ridi, M.S., et al., Gonadotrophic Hormones in Pollen Grains of the Date Palm, Z Naturforsch B., Jan. 1960; 15B: 45-9.
Hassan, A., et al., An Oestrogenic Substance in Pollen-Grains of Date Palm Tree Phoenix dactylifera L., Palmae, Nature, Mar. 22, 1947; 159(4038):409.
Hess, R.A., Estrogen in the Adult Male Rat Reproductive Tract: A Review, Reprod Biol Endocrinol, Jul. 9, 2003; 1:52.
Mahran, G.H., et al., A Phytochemical Study of Date Palm Pollen, Planta Med., 1976; 29(2): 171-175.
Soliman, F.A., et al., The Gonadotrophic Activity of Date Palm Pollen Grains, Experientia, Oct. 15, 1957; 13(10):411-12.
Schroeder, P., et al., Photoprotection Beyond Ultraviolet Radiation—Effective Sun Protection has to include Protection Against Infrared A Radiation-induced Skin Damage, Skin Pharmacol Physiol, 2010:23(1): 15-7.
Thiele, J., et al., Oxidants and Antioxidants in Cutaneous Biology, Current Problems in Dermatology, 1996; vol. 29: 137.
Werner, N., et al., Sex Hormones Save our Skin: The Vascular Networking of Estrogen, Circulation Research, 2009; 104:135.
PCT/US2012/043653, dated Aug. 22, 2010, International Search Report (1 pg.).
Abbas et al., Estradiol, Esteriol Estone and Novel Flavonoids from Date Palm Pollen, Australian Journal of Basic and Applied Sciences, 2011; 5(8):606-614.
Naidu et al., Chemotherapy-induced and/or Radiation Therapy-induced Oral Mucositis—Complicating the Tretament of Cancer, Neoplasia, 2004; 6(5):423-431.
Office Action dated Jun. 25, 2014in U.S. Appl. No. 13/539,855.
Third-Party Submission under 37 CFR 1.290 in U.S. Appl. No. 13/539,855, dated Apr. 2, 2013.
Al-Baltar, Al-Jaam'e-li-Mufradaat-al-Advia-Aghzia, Published by Magba Amra Cairo, Egypt, India, 1874, including translation and statement of relevance as submitted with Third-Party Submission on Apr. 2, 2013 in U.S. Appl. No. 13/539,855.
Khan, Muheet Azam vol. II (Part II), 1898, Published by Matba Nizami, Kanpur, India, including translation and statement of relevance as submitted with Third-Party Submission on Apr. 2, 2013 in U.S. Appl. No. 13/539,855.
Al-Baltar, Al-Jaam-e-li-Mufradaat-al-advia-wal-Aghzia, Published by Magba Amra Cairo, Egypt, India, 1874, including translation and statement of relevance as submitted with Third-Party Submission on Apr. 2, 2013 in U.S. Appl. No. 13/539,855.
Madhava, Ayurvedaprakasah, 1999, Published by Chaukhamba Bharati Academy, Varanasi, India, including translation and statement of relevance as submitted with Third-Party Submission on Apr. 2, 2013 in U.S. Appl. No. 13/539,855.

(Continued)

Primary Examiner — Chris R Tate
(74) Attorney, Agent, or Firm — Jill A. Jacobson

(57) ABSTRACT

Compositions are provided that include date palm pollen or an extract thereof. The compositions may be formulated use in methods of treatment or prophylaxis of inflammatory conditions such as adverse side effects of anti-cancer treatment or stomatitis conditions.

8 Claims, No Drawings

(56) References Cited

OTHER PUBLICATIONS

Vagabhata, Astanga Hrdaya, Boga Munivar Valthyam, 1998, Published by Chaukhamba Orientalia, Varanasi, India, including translation and statement of relevance as submitted with Third-Party Submission on Apr. 2, 2013 in U.S. Appl. No. 13/539,855.

Bogar, Boga Munivar Valthyam—700, Published by B. Rathina Nayakar Sons, Chennai, India, including translation and statement of relevance as submitted with Third-Party Submission on Apr. 2, 2013 in U.S. Appl. No. 13/539,855.

Bharata Bhalsajya Ratnakara vol. V, 1999, Published by B. Jain Pblishers, New Delhi, India, including translation and statement of relevance as submitted with Third-Party Submission on Apr. 2, 2013 in U.S. Appl. No. 13/539,855.

Nighanturatnakarah, 1867, Published by Bishnu Vasudev Godbole, Bombay, India, including translation and statement of relevance as submitted with Third-Party Submission on Apr. 2, 2013 in U.S. Appl. No. 13/539,855.

Bhairava, Anandakandah, 1952, Published by T.M.S.S.M. Library, Madras, India, including translation and statement of relevance as submitted with Third-Party Submission on Apr. 2, 2013 in U.S. Appl. No. 13/539,855.

Alqarni, A., Influence of Some Protein Diets and Some Physiological Conditions of Honeybee Apis mellifera L. Workers, 2006; 6(4):734-37.

Sak, K., Chemotherapy and Dietary Phytochemical Agents, Chemotherapy Research and Practice, Hindawi Publishing Corporation, 2012.

Trueb, R. Chemoherapy-induced Hair Loss, Skin Therapy Lett, Jul.-Aug. 2010; 15(7):5-7.

Bishr, M. et al., Comparitive Study of the Nutritional Value of Four Types of Egyptian Palm Pollens, Journal of Pharmacy and Nutrition Sciences, 2012; 2:50-56.

El Ridi, et al., Isolation of Rutin from the Pollen Grain of the Date Palm (Dactylifera Palma L), Arch Biochem Biophys, Aug. 1952; 39(2):317-21.

\* cited by examiner

PALM POLLEN FOR TREATMENT OF MUCOSITIS AND INFLAMMATORY CONDITIONS

CROSS-REFERENCE TO RELATED APPLICATIONS

This application claims the benefit of U.S. Provisional Application No. 61/834,805, filed on Jun. 13, 2013, which is incorporated herein by reference in its entirety.

FIELD OF THE INVENTION

The invention relates to use of palm pollen for treatment of the side effects of anticancer treatment and other inflammatory conditions.

BACKGROUND

The desired goal of chemotherapy and/or radiation is to eliminate rapidly-dividing cancerous tumor cells. However, a diverse range of non-malignant less rapidly-dividing cells (such as epithelial cells in the gastrointestinal mucosa and cells lining the hair follicles) is also damaged by this approach. These therapies result in many adverse effects in multiple organ systems. Such debilitating effects and toxicities are a major clinical problem and often limit the usefulness of anticancer agents.

The most common complaints of cancer patients undergoing cytotoxic therapy are fatigue, nausea, vomiting, diarrhea, mucositis, and hair loss. If severe enough, adverse side effects can limit a patient's ability to tolerate the dosage and/or duration of treatment of their prescribed anti-cancer regimen.

Mucositis is characterized by the damage to the epithelium of the oropharyngeal cavity and gastrointestinal tract. Chemotherapy and radiotherapy-induced oral mucositis represents a therapeutic challenge frequently encountered in cancer patients. This debilitating side effect causes significant morbidity and may delay the treatment plan as well as increasing therapeutic expenses. Although there are many traditional forms of treatment, such as mouthwashes and local anesthetics, most are ineffective. Antimicrobial agents have not demonstrated consistent efficacy in the prevention or treatment of oral mucositis. Many agents such as topical sucralfate, topical granulocyte macrophage colony stimulating factors (GM-CSF), prostaglandin-E analogue misoprostol, topical corticosteroids, and parenteral radio-protector amifostine have been tried with varying response rates.

New treatment options for the prophylaxis or management of oral mucositis or other inflammatory effects of anti-cancer treatment are needed.

BRIEF SUMMARY OF THE INVENTION

Methods and compositions are provided for treatment or prevention of side effects of anti-cancer treatment, stomatitis, or other inflammatory conditions, such as inflammation of the gastrointestinal tract, and/or for providing supplemental nutrition to individuals in need thereof. The methods disclosed herein include oral or topical administration of palm pollen or an extract thereof from a palm species of the genus *Phoenix*, such as *Phoenix dactylefera* L.

In one aspect, a method is provided for treating, preventing, or ameliorating at least one adverse side effect of chemotherapy or radiation treatment for cancer in an individual in need thereof. The method includes administering pollen from a palm species of the genus *Phoenix* or an extract thereof to the individual (e.g., a composition containing a unit dose of pollen from a palm species of the genus *Phoenix* or an extract thereof).

In some embodiments, the side effect(s) of chemotherapy or radiation treatment that benefit from administration of palm pollen or an extract thereof, as disclosed herein, include, but are not limited to, mucositis, stomatitis, nausea, vomiting, decreased appetite, inflammation of the gastrointestinal tract, and/or alopecia.

In some embodiments, a unit dose of palm pollen or extract thereof is about 0.05 g to about 6 g of palm pollen. In some embodiments, a total daily dose of about 0.1 g to about 6 g of palm pollen or extract thereof is administered. For example, in some embodiments, oral administration includes a total daily dose of any of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 g of palm pollen, or an equivalent amount of an extract thereof, formulated for oral administration in one or more doses per day. In another example, in some embodiments, topical administration includes a total daily dose of about 0.10, 0.15, 0.20, 0.25, 0.30, 0.35, or 0.40 g of palm pollen, or an equivalent amount of an extract thereof, formulated for topical administration in one or more doses per day.

In various embodiments, the composition is formulated as a powder, an effervescent powder, a tablet, an effervescent tablet, a capsule, a spray (e.g., aerosol), or a suspension. In some embodiments, the method includes orally administering about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 per day of palm pollen, or an equivalent amount of extract thereof, in a liquid suspension, a powder, an effervescent powder, a tablet, an effervescent tablet, or a capsule formulation, wherein the administration prevents, treats, or ameliorates oral mucositis, stomatitis, nausea, vomiting, decreased appetite, inflammation of the gastrointestinal tract, and/or alopecia. A unit dose for oral administration in a liquid suspension, a powder, an effervescent powder, a tablet, an effervescent tablet, or a capsule formulation may contain any of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 of palm pollen, or an equivalent amount of extract thereof.

In some embodiments, the method includes orally administering about 0.10, 0.15, 0.20, 0.25, 0.30, 0.35, or 0.40 g of palm pollen, or an equivalent amount of extract thereof per day, in an aerosol or other type of spray formulation, wherein the spray (e.g., aerosol spray) is directed to areas of inflammation in the oral cavity of the individual, and the administration treats and/or ameliorates oral mucositis and/or stomatitis in the individual. A unit dose for oral administration in an aerosol or other type of spray formulation may contain any of about 0.05, 0.10, 0.15, 0.20, 0.25, 0.30, 0.35, or 0.40 g of palm pollen, or an equivalent amount of extract thereof.

In some embodiments, oral administration of palm pollen or extract thereof commences prior (e.g., at least one day prior) to initiation of chemotherapy or radiation treatment and continues through at least a portion of the course of treatment, through the entire course of treatment, or through the entire course of treatment and continuing after cessation of treatment. In other embodiments, administration of palm pollen or extract thereof commences at (e.g., simultaneously or essentially simultaneously with) initiation of chemotherapy or radiation treatment and continues through at least a portion of the course of treatment, through the entire course of treatment, or through the entire course of treatment and continuing after cessation of treatment.

In some embodiments, the method includes topically administering about 0.10, 0.15, 0.20, 0.25, 0.30, 0.35, or 0.40 g of palm pollen, or an equivalent amount of extract thereof per day to the scalp in a spray formulation (e.g., an aerosol) or a suspension (e.g., a shampoo or hair care product), wherein the administration prevents alopecia. A unit dose for topical administration to the scalp in an aerosol or other type of spray formulation or in a suspension may contain any of about 0.05, 0.10, 0.15, 0.20, 0.25, 0.30, 0.35, or 0.40 g of palm pollen, or an equivalent amount of extract thereof.

In some embodiments, topical administration of palm pollen or extract thereof to the scalp of an individual commences prior (e.g., at least one day prior) to initiation of chemotherapy or radiation treatment and continues through at least a portion of the course of treatment, through the entire course of treatment, or through the entire course of treatment and continuing after cessation of treatment. In other embodiments, administration of palm pollen or extract thereof commences at (e.g., simultaneously or essentially simultaneously with) initiation of chemotherapy or radiation treatment and continues through at least a portion of the course of treatment, through the entire course of treatment, or through the entire course of treatment and continuing after cessation of treatment.

In another aspect, a method is provided for providing supplemental nutrition to an individual in need thereof. The method includes orally administering palm pollen from a palm species of the genus *Phoenix* or an extract thereof (e.g., a composition containing a unit dose of pollen from a palm species of the genus *Phoenix* or an extract thereof) to the individual. In some embodiments, the palm pollen or extract thereof is from *Phoenix dactylefera* L.

In various embodiments, the palm pollen or extract thereof is formulated as a powder, an effervescent powder, a tablet, an effervescent tablet, a capsule, or a suspension. In some embodiments, the method includes orally administering about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 per day of palm pollen, or an equivalent amount of extract thereof, in a liquid suspension, a powder, an effervescent powder, a tablet, an effervescent tablet, or a capsule formulation, wherein the administration provides supplemental nutrition to the individual. A unit dose for oral administration in a liquid suspension, a powder, an effervescent powder, a tablet, an effervescent tablet, or a capsule formulation may contain any of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 of palm pollen, or an equivalent amount of extract thereof.

In some embodiments, administration of palm pollen or an extract thereof provides at least one beneficial effect to the individual, such as improved energy, decreased fatigue, improved appetite, or hormone (e.g., estrogen) replacement. In various embodiments, supplemental nutrition may be provided by substances within the palm pollen or extract thereof, including, but not limited to, natural lipids, estrogens, rutin, triterpenoids, carotenoids, minerals, vitamins, and/or amino acids (e.g., essential and/or non-essential amino acids).

In some embodiments, administration of palm pollen or an extract thereof to provide supplemental nutrition occurs prior to, in conjunction with, and/or subsequent to chemotherapy or radiation treatment for cancer. In some embodiments, administration of palm pollen or extract thereof to provide supplemental nutrition to an individual commences prior (e.g., at least one day prior) to initiation of chemotherapy or radiation treatment and continues through at least a portion of the course of treatment, through the entire course of treatment, or through the entire course of treatment and continuing after cessation of treatment. In other embodiments, administration of palm pollen or extract thereof commences at (e.g., simultaneously or essentially simultaneously with) initiation of chemotherapy or radiation treatment and continues through at least a portion of the course of treatment, through the entire course of treatment, or through the entire course of treatment and continuing after cessation of treatment. In some embodiments, administration of palm pollen or extract thereof commences after chemotherapy or radiation therapy has concluded.

In another aspect, a method is provided for treating, preventing, or ameliorating stomatitis in an individual in need thereof. The method includes orally administering palm pollen from a palm species of the genus *Phoenix* or an extract thereof (e.g., a composition containing a unit dose of palm pollen from a palm species of the genus *Phoenix* or an extract thereof) to the individual. In some embodiments, the palm pollen or extract thereof is from *Phoenix dactylefera* L.

In some embodiments, stomatitis conditions that benefit from administration of palm pollen or an extract thereof, as disclosed herein, include, but are not limited to, gingivitis, denture stomatitis, physical stomatitis, xerostomia-induced stomatitis, contact stomatitis, and/or trauma from oral surgery and/or tooth extraction.

In some embodiments, a unit dose of palm pollen or extract thereof is about 0.05 g to about 6 g of palm pollen. In some embodiments, a total daily dose of about 0.1 g to about 6 g of palm pollen or extract thereof is administered. For example, in some embodiments, oral administration includes a total daily dose of any of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 g of palm pollen, or an equivalent amount of an extract thereof, is formulated for oral administration in one or more doses per day.

In various embodiments, a composition containing palm pollen or an extract thereof is formulated as a powder, an effervescent powder, a tablet, an effervescent tablet, a capsule, a suspension, a mouthwash, a toothpaste, a lozenge, or a spray (e.g., aerosol). In some embodiments, the method includes orally administering about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 per day of palm pollen, or an equivalent amount of extract thereof, in a liquid suspension, a powder, an effervescent powder, a tablet, an effervescent tablet, a capsule a suspension, a mouthwash, a toothpaste, a lozenge, or a spray (e.g., aerosol) formulation, wherein the administration prevents, treats, or ameliorates stomatitis, including, but not limited to, gingivitis, denture stomatitis, physical stomatitis, xerostomia-induced stomatitis, contact stomatitis, and/or trauma from oral surgery and/or tooth extraction. A unit dose for oral administration in a powder, an effervescent powder, a tablet, an effervescent tablet, a capsule a suspension, a mouthwash, a toothpaste, or a lozenge may include 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 of palm pollen, or an equivalent amount of extract thereof.

In some embodiments, the method includes orally administering about 0.10, 0.15, 0.20, 0.25, 0.30, 0.35, or 0.40 g of palm pollen, or an equivalent amount of extract thereof per day, in a spray (e.g., aerosol) formulation, wherein the spray (e.g., aerosol) is directed to areas of inflammation in the oral cavity of the individual, and the administration treats and/or ameliorates stomatitis in the individual. A unit dose for oral administration in a spray (e.g., aerosol) formulation may contain any of about 0.05, 0.10, 0.15, 0.20, 0.25, 0.30, 0.35, or 0.40 g of palm pollen, or an equivalent amount of extract thereof.

In another aspect, compositions are provided that contain palm pollen or an extract thereof, formulated for oral or topical administration in a method disclosed herein. The compositions may contain palm pollen or an extract thereof from a palm species of the genus *Phoenix*, formulated for oral administration as a liquid suspension, a powder, an effervescent powder, a tablet, an effervescent tablet, a capsule a suspension, a mouthwash, a toothpaste, a lozenge, or a spray (e.g., aerosol). In some embodiments, the palm pollen or extract thereof is from *Phoenix dactylefera* L.

In various embodiments, a composition for oral administration in the form of a powder, an effervescent powder, a tablet, an effervescent tablet, a capsule a suspension, a mouthwash, a toothpaste, or a lozenge may contain a unit dose containing any of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 of palm pollen, or an equivalent amount of extract thereof. In some embodiments, a composition in the form of an aerosol or other type of spray formulation for oral administration may contain a unit dose containing any of about 0.05, 0.10, 0.15, 0.20, 0.25, 0.30, 0.35, or 0.40 g of palm pollen, or an equivalent amount of extract thereof.

In some embodiments, a composition for topical administration in the form of an aerosol or other type of spray formulation, or a suspension, such as a shampoo or hair product, may contain a unit dose containing any of about 0.05, 0.10, 0.15, 0.20, 0.25, 0.30, 0.35, or 0.40 g of palm pollen, or an equivalent amount of extract thereof.

DETAILED DESCRIPTION

Formulations and methods for treatment of adverse side effects of chemotherapy and radiation treatment for cancer and/or stomatitis and/or gastrointestinal inflammation, and formulations and methods for providing supplemental nutrition to an individual in need thereof, such as an individual undergoing chemotherapy or radiation treatment, are provided. The formulations described herein include palm pollen or an extract thereof.

Definitions

Numeric ranges provided herein are inclusive of the numbers defining the range.

"A," "an" and "the" include plural references unless the context clearly dictates otherwise.

The terms "DPP," "date palm pollen," or "palm pollen," used interchangeably herein, refer to pollen from a species of the genus *Phoenix* in the family Palmae. The term "date palm" as used herein includes both ornamental and fruit-producing species in the genus *Phoenix*. As used herein, the term an "extract" of DPP refers to material that has been extracted from pollen from a species of the genus *Phoenix*.

The term "derived from" encompasses the terms "originated from," "obtained from," "obtainable from," "isolated from," and "created from," and generally indicates that one specified material finds its origin in another specified material or has features that can be described with reference to the another specified material.

"Unit dose" refers to an amount of a substance contained in a formulation for administration in a method as described herein that is sufficient to provide a therapeutic or prophylactic effect in an individual to whom it is administered. A unit dose may be administered in a single administration (e.g., oral or topical administration) of the formulation or in two or more administrations. A unit dose may contain a therapeutically or prophylactically effective amount of the substance to be administered.

"Therapeutically effective amount" refers to an amount of a substance that will render a desired therapeutic outcome (for example, reduction or elimination of one or more adverse side effect of chemotherapy or radiation treatment for cancer).

"Prophylactically effective amount" refers to an amount of a substance sufficient to prevent or reduce severity of a disease or symptom (for example, prevention or reduction in severity of one or more adverse side effect of chemotherapy or radiation treatment for cancer).

An "individual" refers to a mammal, such as a human.

Date Palm Pollen

The compositions and methods described herein include pollen from a palm in the genus *Phoenix* and/or an extract thereof. In some embodiments, pollen from a date palm is used. In one exemplary embodiment, the formulations herein include pollen from the species *Phoenix dactylifera* L, Palmae. The pollen can be harvested from male date palm trees during the flowering season in the months of February and March.

Pollen grains have been designed by nature to transfer genetic material from plant-to-plant. Date palm pollen (DPP) exists in a very fine powder material, produced by the male flowering date palm. The male flower develops 2-3 weeks before the female flower. Once the male pods open, they may be removed from the tree and dried. Once dried, pollen may be stored in a cool environment. DPP represents the reproductive cell of the male flower and contains the male contribution to the next generation of the plant.

Physico-Chemical Characteristics

DPP has unique size, shape and surface characteristics. Physico-chemical interaction of DPP with a biological surface may depend, for example, on particle size, micromorphology, and/or surface geometry. Properties like flow, adhesion, and biochemical interactions with body surfaces may be under the influence of any or all of these characteristics.

The size of DPP pollen grains is between 20 to 75 microns, for example, about 20, 25, 30, 35, 40, 45, 50, 55, 60, 65, 70, or 75 microns. In one embodiment, DPP has an average diameter of about 24 microns. For example, in one embodiment, DPP is from the species *Phoenix dactylifera* L, Palmae and has a diameter of about 21 to about 27 microns, e.g., about 21, 22, 23, 24, 25, 26, or 27 microns, for example, a mean diameter of about 24 microns.

The shape is frequently elliptical. The surface is reticulate with irregular semi-circular pores and covered with spikes or needle like structures. The tip edges of the spikes are in the submicron range.

Dry DPP powder has excellent flow properties in addition to excellent spreading and adhesion properties on surfaces. DPP has both adhesive and spreading properties when applied to body surfaces. The flow properties of freshly-collected pollen depend on its moisture content; when dry, it is free flowing. The flow properties can be regulated by the addition of one or more flow regulating agent(s). Surface ruggedness of palm pollen permits it to adhere easily to biological surfaces. The spikes present on the surface allow the pollen to adhere to complex surface geometry and reach difficult-to-reach cracks on the skin surface.

Phytochemical Characteristics

Early investigations revealed that DPP contains estrone. (Hassan and Abou el Wafa (1947) *Nature* 159(4038): 409) More recent studies have confirmed the presence of all three major naturally-occurring estrogens (estrone, estradiol, and estriol) are present in DPP. (Fawkeya and Ateya (2011) *Australian Journal of Basic and Applied Science* 5(8): 606-614) DPP also contains rutin, a glycoside combination of the flavonol quercetin and the disaccharide rutinose that acts as an antioxidant. DPP also contains carotenoids, which are efficient free-radical scavengers, known to enhance the vertebrate immune system. A glycoprotein with gonadotrophic activity has been isolated from DPP. (Mahran et al. (1976) *Planta Med.* 29(2):171-175; El Ridi et al. (1952) *Arch Biochem Biophys* 39(2):317-21) DPP also contains triterpenoids (e.g., beta-amyrin), natural lipids (e.g., esters of palmitic, linoleic, and myristic acid), minerals (e.g., magnesium, phosphorous, sulfur, potassium, calcium, zinc, and/or manganese, vitamins (e.g., vitamin $B_1$, $B_2$, and/or $B_{12}$), and/or amino acids (e.g., essential amino acids (e.g., threonine, valine, methionine, isoleucine, leucine, phenylalanine, histidine, and/or lysine) and/or non-essential amino acids (e.g., aspartic acid, glutamic acid, proline, glycine, alanine, tyrosine, arginine, and/or serine).

Compositions

Compositions are provided that include palm pollen or an extract thereof, as described above. The form and components to be included in the composition will depend on the site of administration and intended use of the composition, as will be readily apparent to those of skill in the art. In some embodiments, a formulation for oral administration that contains palm pollen or an extract thereof may be provided for prevention, treatment, and/or amelioration of at least one side effect of chemotherapy and/or radiation treatment for cancer, such as, but not limited to, mucositis (e.g., oral mucositis), nausea, vomiting, decreased appetite, inflammation of the gastrointestinal tract, and/or alopecia. In other embodiments, a formulation for topical administration that contains palm pollen or an extract thereof may be provided for prevention of alopecia (e.g., alopecia induced by chemotherapy or radiation treatment for cancer). In further embodiments, a formulation for oral administration that contains palm pollen or an extract thereof may be provided for supplemental nutrition to an individual in need thereof, such as an individual undergoing chemotherapy or radiation treatment for cancer or any individual for which such supplementation would be beneficial, such as an individual with a disorder or disease condition that requires supplemental nutrition, including, but not limited to, an individual with an inflammatory bowel disease (e.g., Crohn's disease, ulcerative colitis, irritable bowel syndrome). In further embodiments, a formulation for oral administration that contains palm pollen or an extract thereof may be provided for prevention, treatment, and/or amelioration of stomatitis (e.g., gingivitis, denture stomatitis, physical stomatitis, xerostomia-induced stomatitis, contact stomatitis, and/or trauma from oral surgery and/or tooth extraction). In further embodiments, a formulation for oral administration that contains palm pollen or an extract thereof may be provided for prevention, treatment, and/or amelioration of inflammation of the gastrointestinal tract.

For oral applications of use, a composition herein may be formulated in any convenient form for oral administration. For example, the composition may be formulated as a powder, an effervescent powder, a suspension, a tablet, an effervescent tablet, a capsule, a spray (e.g., aerosol), a toothpaste, or a mouthwash, or any composition that may be orally administered to an individual, for delivery of palm pollen or an extract thereof, and/or delivery of a substance, for example, a substance contained in palm pollen. In some embodiments, a composition is formulated for oral delivery of a unit dose of palm pollen, an extract thereof, or one or more compounds present in or derived from palm pollen, to an individual. A unit dose for oral administration may contain, for example, about 0.1 g to about 6 g of palm pollen or an equivalent amount of an extract thereof (e.g., an amount of palm pollen extract that is derived from about 0.1 g to about 6 g of palm pollen; for example, an amount of palm pollen extract that is equivalent to 0.1 g of palm pollen is an amount of extract that is derived (e.g., extracted from) from 0.1 g of palm pollen), per day, although a higher or lower amount may be administered depending on the individual and application of use. In some embodiments, a total daily dose of any of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 g of palm pollen, or an equivalent amount of an extract thereof, is formulated for oral administration in one or more doses per day. In some embodiments, a unit dose that is formulated for oral administration may contain, for example, about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 g of palm pollen, or an equivalent amount of an extract thereof.

In some embodiments, a total daily dose of any of about 0.1 g to about 6.0 g, about 0.5 g to about 6.0 g, about 1.0 g to about 6.0 g, about 1.5 g to about 6.0 g, about 2.0 g to about 6.0 g, about 2.5 g to about 6.0 g, about 3.0 g to about 6.0 g, about 3.5 g to about 6.0 g, about 4.0 g to about 6.0 g, about 4.5 g to about 6.0 g, about 5.0 g to about 6.0 g, about 5.5 g to about 6.0 g, about 0.1 g to about 0.5 g, about 0.1 g to about 1.0 g, about 0.1 g to about 2.0 g, about 0.1 g to about 2.5 g, about 0.1 g to about 3.0 g, about 0.1 g to about 3.5 g, about 0.1 g to about 4.0 g, about 0.1 g to about 4.5 g, about 0.1 g to about 5.0 g, about 0.1 g to about 5.5 g, about 0.1 g to about 0.05 g, about 0.5 g to about 1.0 g, about 1.0 g to about 1.5 g, about 1.5 g to about 2.0 g, about 2.5 g to about 3.0 g, about 3.0 g to about 3.5 g, about 3.5 g to about 4.0 g, about 4.0 g to about 4.5 g, about 4.5 g to about 5.0 g, about 5.5 g to about 6.0 g, about 0.1 g to about 1.0 g, about 1.0 g to about 2.0 g, about 2.0 g to about 3.0 g, about 3.0 g to about 4.0 g, about 4.0 g to about 5.0 g, about 5.0 g to about 6.0 g, about 0.1 g to about 1.5 g, about 1.0 g to about 3.0 g, about 2.0 g to about 4.0 g, about 3.0 g to about 5.0 g, about 1.5 g to about 3.0 g, about 2.5 g to about 5.0 g, or about 3.5 g to about 6.0 g of palm pollen, or an equivalent amount of an extract thereof, is formulated for oral administration in one or more doses per day.

In some embodiments, a unit dose that is formulated for oral administration may contain, for example, any of about 0.1 g to about 6.0 g, about 0.5 g to about 6.0 g, about 1.0 g to about 6.0 g, about 1.5 g to about 6.0 g, about 2.0 g to about 6.0 g, about 2.5 g to about 6.0 g, about 3.0 g to about 6.0 g, about 3.5 g to about 6.0 g, about 4.0 g to about 6.0 g, about 4.5 g to about 6.0 g, about 5.0 g to about 6.0 g, about 5.5 g to about 6.0 g, about 0.1 g to about 0.5 g, about 0.1 g to about 1.0 g, about 0.1 g to about 2.0 g, about 0.1 g to about 2.5 g, about 0.1 g to about 3.0 g, about 0.1 g to about 3.5 g, about 0.1 g to about 4.0 g, about 0.1 g to about 4.5 g, about 0.1 g to about 5.0 g, about 0.1 g to about 5.5 g, about 0.1 g to about 0.05 g, about 0.5 g to about 1.0 g, about 1.0 g to about 1.5 g, about 1.5 g to about 2.0 g, about 2.5 g to about 3.0 g, about 3.0 g to about 3.5 g, about 3.5 g to about 4.0 g, about 4.0 g to about 4.5 g, about 4.5 g to about 5.0 g, about 5.5 g to about 6.0 g, about 0.1 g to about 1.0 g, about 1.0 g to about 2.0 g, about 2.0 g to about 3.0 g, about 3.0 g to about 4.0 g, about 4.0 g to about 5.0 g, about 5.0 g to about 6.0 g, about 0.1 g to about 1.5 g, about 1.0 g to about 3.0 g, about 2.0 g to about 4.0 g, about 3.0 g to about 5.0 g, about 1.5 g to about 3.0 g, about 2.5 g to about 5.0 g, or about 3.5 g to about 6.0 g of palm pollen, or an equivalent amount of an extract thereof.

For topical applications of use, a composition herein may be formulated in any convenient form for topical administration. For example, the composition may be formulated as a spray (e.g., aerosol), suspension, shampoo, hair care product, or any composition that may be topically administered to an individual, for example, for topical delivery of palm pollen or an extract thereof, and/or delivery of a substance, for example, a substance contained in palm pollen. For example, a topical formulation disclosed herein may be topically applied to the scalp of an individual. In some embodiments, a composition is formulated for topical delivery of a unit dose of palm pollen, an extract thereof, or one or more compounds present in or derived from palm pollen, to an individual. A unit dose for topical administration may contain, for example, about 0.05 g to about 0.4 g of palm pollen (e.g., DPP) or an equivalent amount of an extract thereof (e.g., an amount of palm pollen extract that is derived from about 0.05 g to about 0.4 g of palm pollen; for example, an amount of palm pollen extract that is equivalent to 0.05 g of palm pollen is an amount of extract that is derived (e.g., extracted from) from 0.05 g of palm pollen), or one or more compounds that is present in or derived from palm pollen, per day, although a higher or lower amount may be administered depending on the individual and application of use. In some embodiments, a total daily dose of about 0.10, 0.15, 0.20, 0.25, 0.30, 0.35, or 0.40 g of palm pollen, or an equivalent amount of an extract thereof, is formulated for topical administration in one or more doses per day. In some embodiments, a unit dose for topical administration may contain, about 0.05, 0.10, 0.15, 0.20, 0.25, 0.30, 0.35, or 0.40 g of palm pollen, or an equivalent amount of an extract thereof.

In some embodiments, a total daily dose of any of about 0.05 g to about 0.40 g, about 0.10 g to about 0.40 g, about 0.15 g to about 0.40 g, about 0.20 g to about 0.40 g, about 0.25 g to about 0.40 g, about 0.30 g to about 0.40 g, about 0.35 g to about 0.40 g, about 0.05 g to about 0.10 g, about 0.05 g to about 0.15 g, about 0.05 g to about 0.20 g, about 0.05 g to about 0.25 g, about 0.05 g to about 0.30 g, about 0.05 g to about 0.35 g, about 0.10 to about 0.15 g, about 0.15 g to about 0.20 g, about 0.20 g to about 0.25 g, about 0.25 g to about 0.30 g, about 0.30 g to about 0.35 g, about 0.35 g to about 0.40 g, about 0.10 g to about 0.25 g, about 0.15 g to about 0.30 g, about 0.20 g to about 0.35 g, about 25 g to about 0.40 g, about 0.10 g to about 0.30 g, or about 0.20 g to about 0.40 g of palm pollen, or an equivalent amount of an extract thereof, is formulated for topical administration in one or more doses per day.

In some embodiments, a unit dose that is formulated for topical administration may contain, for example, any of about 0.05 g to about 0.40 g, about 0.10 g to about 0.40 g, about 0.15 g to about 0.40 g, about 0.20 g to about 0.40 g, about 0.25 g to about 0.40 g, about 0.30 g to about 0.40 g, about 0.35 g to about 0.40 g, about 0.05 g to about 0.10 g, about 0.05 g to about 0.15 g, about 0.05 g to about 0.20 g, about 0.05 g to about 0.25 g, about 0.05 g to about 0.30 g, about 0.05 g to about 0.35 g, about 0.10 to about 0.15 g, about 0.15 g to about 0.20 g, about 0.20 g to about 0.25 g, about 0.25 g to about 0.30 g, about 0.30 g to about 0.35 g, about 0.35 g to about 0.40 g, about 0.10 g to about 0.25 g, about 0.15 g to about 0.30 g, about 0.20 g to about 0.35 g, about 25 g to about 0.40 g, about 0.10 g to about 0.30 g, or about 0.20 g to about 0.40 g of palm pollen, or an equivalent amount of an extract thereof.

In some embodiments of the formulations described herein, an extract of palm pollen is used. An extract may be prepared, for example, by extraction of one or more constituent(s), or all or substantially all constituents, of the pollen with one or more organic solvent(s). Extraction may be followed by evaporation, purification, and/or drying of the extract prior to incorporation into a formulation. A DPP extract may contain one or more components of DPP and no or substantially no intact pollen grains. In some embodiments, a formulation as described herein may contain both DPP and an extract of DPP.

Typically, in addition to the palm pollen or extract thereof, a composition herein includes one or more additional constituents to facilitate administration, such as flow regulator(s), diluent(s), filler(s), anti-adhesive(s), and/or compound(s) that produce an effervescent reaction. In some embodiments, one or more flow regulating agent(s) is included. For example, silica (e.g., colloidal silica), silica gel, magnesium trisilicate, cornstarch, and/or talc may be included as a flow regulating agent. A flow regulating agent may be included to increase flow of the formulation, depending on the application of use. A powder, tablet, or capsule formulation may include one or more such flow regulating agent(s). A tablet or capsule formulation may further contain one or more diluent(s), such as spray dried lactose and/or starch, and/or one or more anti-adhesive substance(s), such as magnesium stearate, talc, and/or stearic acid. Effervescent formulations, such as effervescent powders or tablets, may further contain compounds to produce an effervescent reaction, for example, when dissolved in water, e.g., acid and base components such as tartaric acid, citric acid, and sodium bicarbonate. An aerosol formulation may contain one or more propellant(s) to facilitate pressurized packing of the composition, such as dichlorodifluoromethane (Propellant 12). In some embodiments, one or more flavoring or fragrance substance may be included as suitable for the application of use (e.g., flavoring for oral administration or fragrance for topical administration).

In some embodiments, the composition is formulated as a powder, and in addition to palm pollen or an extract thereof, the powder formulation may contain one or flow regulator(s), such as silica (e.g., colloidal silica), silica gel, magnesium trisilicate, cornstarch, and/or talc. The powder formulation may be suspended in a liquid, such as water, prior to administration, e.g., oral administration.

In some embodiments, the composition is formulated as an effervescent powder, and in addition to palm pollen or an extract thereof, the effervescent powder may contain one or more diluent(s), such as spray dried lactose and/or starch, and compound(s) that will produce an effervescent reaction when the powder is dissolved in a suitable liquid for the effervescent reaction to occur, such as water or other aqueous media (e.g., juice, milk, etc.). A nonlimiting example of compounds that will produce such an effervescent reaction is tartaric acid, citric acid, and sodium bicarbonate. An effervescent powder formulation may optionally include one or more flavoring substance (e.g., mint, fruit flavor, chocolate, etc).

In some embodiments, the composition is formulated as a tablet, and in addition to palm pollen or an extract thereof, the tablet may contain one or more diluent(s), such as spray dried lactose and/or starch, and one or more anti-adhesive(s), such as magnesium stearate, talc, and/or stearic acid.

In some embodiments, the composition is formulated as an effervescent tablet, and in addition to palm pollen or an extract thereof, the tablet may contain one or more diluent(s), such as spray dried lactose and/or starch, one or more anti-adhesive(s), such as magnesium stearate, talc, and/or stearic acid, and one or more flow regulator(s), such as silica (e.g., colloidal silica), silica gel, magnesium trisilicate, cornstarch, and/or talc, and compound(s) that will produce an effervescent reaction when the tablet is dissolved in a suitable liquid for the effervescent reaction to occur, such as water or other aqueous media (e.g., juice, milk, etc.). A nonlimiting example of compounds that will produce such an effervescent reaction is tartaric acid, citric acid, and sodium bicarbonate. An effervescent tablet formulation may optionally include one or more flavoring substance (e.g., mint, fruit flavor, chocolate, etc).

In some embodiments, the composition is formulated in a capsule (e.g., hard gelatin capsule), and in addition to palm pollen or an extract thereof, the tablet may contain one or more diluent(s), such as spray dried lactose and/or starch, and one or more flow regulator(s), such as silica (e.g., colloidal silica), silica gel, magnesium trisilicate, cornstarch, and/or talc.

In some embodiments, the composition is formulated as an aerosol, and in addition to palm pollen or an extract thereof, the aerosol may contain one or more propellant(s), such as dichlorodifluoromethane (Propellant 12).

In some embodiments, the composition is formulated as a suspension for topical administration, and in addition to palm pollen or an extract thereof, the suspension may contain a vehicle or carrier (e.g., suspending media) of appropriate viscosity and having the ability to suspend palm pollen, such as polyethylene glycol (e.g., PEG 400). A topical suspension may optionally include one or more fragrance.

Examples of compositions formulated as described above are provided in Table 1.

TABLE 1

Exemplary DPP Formulations

| Formulation | Components (function) | Amount (g) |
| --- | --- | --- |
| Powder formulation (per 100 g) | Date palm pollen | 99.5 |
| | Colloidal silica (flow regulator) | 0.5 |
| Effervescent powder (per 200 g) | Date palm pollen | 100 |
| | Tartaric acid (effervescent reaction) | 25 |
| | Citric acid (effervescent reaction) | 25 |
| | Sodium bicarbonate (effervescent reaction) | 30 |
| | Spray dried lactose (diluent) | 20 |
| | Optional flavoring agent(s) | QS for desired flavoring effect |
| Tablet (per 2 g) | Date palm pollen | 1 |
| | Spray dried lactose (diluent) | 0.7 |
| | Magnesium stearate (anti-adhesive) | 0.1 |
| | Talc (anti-adhesive) | 0.2 |
| Effervescent tablet (per 2 g) | Date palm pollen | 1 |
| | Sodium bicarbonate (effervescent reaction) | 0.3 |
| | Tartaric acid (effervescent reaction) | 0.2 |
| | Citric acid (effervescent reaction) | 0.2 |
| | Spray dried lactose (diluent) | 0.15 |
| | Magnesium stearate (anti-adhesive) | 0.05 |
| | Talc (anti-adhesive) | 0.05 |
| | Colloidal Silica (flow regulator) | 0.05 |
| | Optional flavoring agent(s) | QS for desired flavoring effect |
| Hard gelatin capsule (per 1.5 g) | Date palm pollen | 1 |
| | Spray dried lactose (diluent) | 0.45 |
| | Colloidal silica (flow regulator) | 0.05 |
| Aerosol (per 100 metered doses) | Date palm pollen | 5 |
| | Propellant 12 (pressurized packing) | 20 |
| Topical suspension (per 100 g) | Date palm pollen | 20 |
| | PEG 400 (99%) (vehicle) | 80 |
| | Optional fragrance | QS for desired fragrance effect |

The formulations described in Table 1 are exemplary and are not intended to be limiting. Other formulations may be prepared with other components and ratios of components by a person of skill in the formulation art and as adapted to have desired properties for a particular application of use. The formulation, manufacturing, and control of oral and topical formulations are known to pharmacists and others in the formulation art and are described in reference texts, such as Lachman L, Leiberman H, and Kanig J "The Theory and Practice of Industrial Pharmacy," published by Lea & Febiger (1986). Ratios of components in the formulations described herein may be adjusted by a person of skill in the formulation art based on optimum amounts necessary to provide maximum flow and/or stability.

In one embodiment, the composition contains DPP and one or more flow regulating agent(s) (e.g., silica (e.g., colloidal silica), silica gel, magnesium trisilicate, cornstarch, and/or talc) in a ratio to provide a powder formulation. Optionally, the composition also contains one or more flavoring agent.

In another embodiment, the composition contains DPP, one or more diluent(s) (e.g., spray dried lactose and/or starch), and compounds suitable for production of an effervescent reaction when the composition is suspended in a liquid such as water (e.g., tartaric acid; citric acid; sodium bicarbonate) in a ratio to provide an effervescent powder. Optionally, the composition also contains one or more flavoring agent.

In another embodiment, the composition contains DPP, one or more diluent(s) (e.g., spray dried lactose and/or starch), and one or more anti-adhesive(s) (e.g., magnesium stearate, talc, and/or stearic acid) in a ratio to provide a tablet (e.g., fast dissolving tablet).

In another embodiment, the composition contains DPP, one or more diluent(s) (e.g., spray dried lactose and/or starch), one or more flow regulator(s) (e.g., silica (e.g., colloidal silica), silica gel, magnesium trisilicate, cornstarch, and/or talc one or more anti-adhesive(s) (e.g., magnesium stearate, talc, and/or stearic acid), and compounds suitable for production of an effervescent reaction when the composition is suspended in a liquid such as water (e.g., tartaric acid; citric acid; sodium bicarbonate) in a ratio to provide an effervescent tablet. Optionally, the composition also contains one or more flavoring agent.

In another embodiment, the composition contains DPP, one or more diluent(s) (e.g., spray dried lactose and/or starch) and one or more flow regulator(s) (e.g., silica (e.g., colloidal silica), silica gel, magnesium trisilicate, cornstarch, and/or talc) in a ratio for inclusion in a capsule, such as a hard gelatin capsule.

In another embodiment, the composition contains DPP and at least one propellant (e.g., dichlorodifluoromethane) in a ratio to provide a pressurized aerosol formulation.

In another embodiment, the composition contains DPP, one or more vehicle or carrier (e.g., polyethylene glycol, such as PEG 400) in a ratio to provide a topical suspension. Optionally, the composition contains one or more fragrance.

Methods of Use

A composition containing palm pollen or an extract thereof, as described above, may be orally administered to an individual in a method in which the composition provides a beneficial effect to the individual. In some embodiments, a composition as described herein may be administered orally in a method for preventing, treating, or ameliorating at least one adverse side effect of chemotherapy or radiation treatment for cancer, including but not limited to, mucositis (e.g., oral mucositis), stomatitis, nausea, vomiting, decreased appetite, inflammation of the gastrointestinal tract, and/or alopecia. In some embodiments, a composition as described herein may be administered orally in a method for preventing, treating, or ameliorating stomatitis, including but not limited to, gingivitis, denture stomatitis, physical stomatitis, xerostomia-induced stomatitis, contact stomatitis, and/or trauma (e.g., inflammation) from oral surgery and/or tooth extraction. In some embodiments, a composition as described herein may be administered orally in a method for preventing, treating, or ameliorating an inflammation, and/or one or more symptom of inflammation, of the gastrointestinal tract. In some embodiments, a composition as described herein may be administered orally in a method for providing supplemental nutrition to an individual (e.g., an individual undergoing chemotherapy or radiation treatment for cancer or any individual for which such supplementation would be beneficial, such as an individual with a disorder or disease condition that requires supplemental nutrition), including but not limited to, providing natural lipids, estrogens (e.g., estrone, estradiol, estriol), rutin, triterpenoids, and/or carotenoids. Beneficial effects that may be provided by such supplemental nutrition include, but are not limited to, improved energy, decreased fatigue, and/or improved appetite.

Examples of formulations that are suitable for oral administration include, but are not limited, to powders, tablets, effervescent formulations such as effervescent powders or tablets, capsules, sprays (e.g., aerosols), suspensions, lozenges, toothpastes, and mouthwashes.

In one embodiment, a composition containing palm pollen as disclosed herein is administered through a feeding tube, e.g., for a patient who cannot swallow and is being fed via a feeding tube.

A composition containing palm pollen or an extract thereof, as described above, may be topically administered to an individual in a method in which the composition provides a beneficial effect to the individual. In some embodiments, a composition as described herein may be administered topically to the scalp of an individual in a method for preventing alopecia (e.g., alopecia resulting from chemotherapy or radiation treatment for cancer). Examples of formulations that are suitable for topical administration include, but are not limited to, sprays (e.g., aerosols), suspensions, shampoos, and hair care products.

A formulation containing a unit dose of DPP or an extract thereof may be administered once per day or more than once per day (e.g., 2, 3, 4, or more times per day). For example, one or more than one dose (e.g., 2, 3, 4, or more doses) may be administered to provide a total daily dose of about 0.1 g to about 6 g of palm pollen or an equivalent amount of extract thereof for oral administration or a total daily dose of about 0.1 to about 0.2 g for topical administration. A total daily dose may contain, for example, about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 g for oral administration or about 0.10, 0.15, 0.20, 0.25, 0.30, 0.35, or 0.40 g for topical administration of palm pollen or an equivalent amount of extract thereof. A unit dose may contain, for example, about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 g for oral administration or about 0.05, 0.10, 0.15, 0.20, 0.25, 0.30, 0.35, or 0.40 g for topical administration of palm pollen or an equivalent amount of extract thereof.

In some embodiments, a total daily dose of any of about 0.1 g to about 6.0 g, about 0.5 g to about 6.0 g, about 1.0 g to about 6.0 g, about 1.5 g to about 6.0 g, about 2.0 g to about 6.0 g, about 2.5 g to about 6.0 g, about 3.0 g to about 6.0 g, about 3.5 g to about 6.0 g, about 4.0 g to about 6.0 g, about 4.5 g to about 6.0 g, about 5.0 g to about 6.0 g, about 5.5 g to about 6.0 g, about 0.1 g to about 0.5 g, about 0.1 g to about 1.0 g, about 0.1 g to about 2.0 g, about 0.1 g to about 2.5 g, about 0.1 g to about 3.0 g, about 0.1 g to about 3.5 g, about 0.1 g to about 4.0 g, about 0.1 g to about 4.5 g, about 0.1 g to about 5.0 g, about 0.1 g to about 5.5 g, about 0.1 g to about 0.05 g, about 0.5 g to about 1.0 g, about 1.0 g to about 1.5 g, about 1.5 g to about 2.0 g, about 2.5 g to about 3.0 g, about 3.0 g to about 3.5 g, about 3.5 g to about 4.0 g, about 4.0 g to about 4.5 g, about 4.5 g to about 5.0 g, about 5.5 g to about 6.0 g, about 0.1 g to about 1.0 g, about 1.0 g to about 2.0 g, about 2.0 g to about 3.0 g, about 3.0 g to about 4.0 g, about 4.0 g to about 5.0 g, about 5.0 g to about 6.0 g, about 0.1 g to about 1.5 g, about 1.0 g to about 3.0 g, about 2.0 g to about 4.0 g, about 3.0 g to about 5.0 g, about 1.5 g to about 3.0 g, about 2.5 g to about 5.0 g, or about 3.5 g to about 6.0 g of palm pollen, or an equivalent amount of an extract thereof, is administered orally in one or more doses per day (e.g., 1, 2, 3, 4, or more doses per day).

In some embodiments, a unit dose of any of about 0.1 g to about 6.0 g, about 0.5 g to about 6.0 g, about 1.0 g to about 6.0 g, about 1.5 g to about 6.0 g, about 2.0 g to about 6.0 g, about 2.5 g to about 6.0 g, about 3.0 g to about 6.0 g, about 3.5 g to about 6.0 g, about 4.0 g to about 6.0 g, about 4.5 g to about 6.0 g, about 5.0 g to about 6.0 g, about 5.5 g to about 6.0 g, about 0.1 g to about 0.5 g, about 0.1 g to about 1.0 g, about 0.1 g to about 2.0 g, about 0.1 g to about 2.5 g, about 0.1 g to about 3.0 g, about 0.1 g to about 3.5 g, about 0.1 g to about 4.0 g, about 0.1 g to about 4.5 g, about 0.1 g to about 5.0 g, about 0.1 g to about 5.5 g, about 0.1 g to about 0.05 g, about 0.5 g to about 1.0 g, about 1.0 g to about 1.5 g, about 1.5 g to about 2.0 g, about 2.5 g to about 3.0 g, about 3.0 g to about 3.5 g, about 3.5 g to about 4.0 g, about 4.0 g to about 4.5 g, about 4.5 g to about 5.0 g, about 5.5 g to about 6.0 g, about 0.1 g to about 1.0 g, about 1.0 g to about 2.0 g, about 2.0 g to about 3.0 g, about 3.0 g to about 4.0 g, about 4.0 g to about 5.0 g, about 5.0 g to about 6.0 g, about 0.1 g to about 1.5 g, about 1.0 g to about 3.0 g, about 2.0 g to about 4.0 g, about 3.0 g to about 5.0 g, about 1.5 g to about 3.0 g, about 2.5 g to about 5.0 g, or about 3.5 g to about 6.0 g of palm pollen, or an equivalent amount of an extract thereof is administered orally.

In some embodiments, a total daily dose of any of about 0.05 g to about 0.40 g, about 0.10 g to about 0.40 g, about 0.15 g to about 0.40 g, about 0.20 g to about 0.40 g, about 0.25 g to about 0.40 g, about 0.30 g to about 0.40 g, about 0.35 g to about 0.40 g, about 0.05 g to about 0.10 g, about 0.05 g to about 0.15 g, about 0.05 g to about 0.20 g, about 0.05 g to about 0.25 g, about 0.05 g to about 0.30 g, about 0.05 g to about 0.35 g, about 0.10 to about 0.15 g, about 0.15 g to about 0.20 g, about 0.20 g to about 0.25 g, about 0.25 g to about 0.30 g, about 0.30 g to about 0.35 g, about 0.35 g to about 0.40 g, about 0.10 g to about 0.25 g, about 0.15 g to about 0.30 g, about 0.20 g to about 0.35 g, about 25 g to about 0.40 g, about 0.10 g to about 0.30 g, or about 0.20 g to about 0.40 g of palm pollen, or an equivalent amount of an extract thereof, is topically administered in one or more doses per day (e.g., 1, 2, 3, 4, or more doses per day).

In some embodiments, a unit dose of any of about 0.05 g to about 0.40 g, about 0.10 g to about 0.40 g, about 0.15 g to about 0.40 g, about 0.20 g to about 0.40 g, about 0.25 g to about 0.40 g, about 0.30 g to about 0.40 g, about 0.35 g to about 0.40 g, about 0.05 g to about 0.10 g, about 0.05 g to about 0.15 g, about 0.05 g to about 0.20 g, about 0.05 g to about 0.25 g, about 0.05 g to about 0.30 g, about 0.05 g to about 0.35 g, about 0.10 to about 0.15 g, about 0.15 g to about 0.20 g, about 0.20 g to about 0.25 g, about 0.25 g to about 0.30 g, about 0.30 g to about 0.35 g, about 0.35 g to about 0.40 g, about 0.10 g to about 0.25 g, about 0.15 g to about 0.30 g, about 0.20 g to about 0.35 g, about 25 g to about 0.40 g, about 0.10 g to about 0.30 g, or about 0.20 g to about 0.40 g of palm pollen, or an equivalent amount of an extract thereof, is topically administered.

A method for treating, preventing, or ameliorating at least one adverse side effect of chemotherapy or radiation treatment for cancer is provided. The method includes orally administering a composition that includes a prophylactically effective or therapeutically effective unit dose of palm pollen or an extract thereof to the individual, wherein at least one adverse side effect, such as mucositis, stomatitis, nausea, vomiting, decreased appetite, inflammation of the gastrointestinal tract, or alopecia, is prevented, reduced, or eliminated. The administration may commence prior to, concurrent with the start of, or after the start of chemotherapy or radiation treatment. The administration may continue concurrently with the entire course of chemotherapy or radiation treatment or with a portion of the course of chemotherapy or radiation treatment, either continuously or intermittently during the course of treatment and/or after chemotherapy or radiation treatment has concluded. In various embodiments, a powder, effervescent powder, tablet, effervescent powder, capsule, spray (e.g., aerosol), or suspension that contains palm pollen or an extract thereof is administered orally. In some embodiments, at least one adverse side effect of chemotherapy or radiation treatment, such as mucositis, stomatitis, nausea, vomiting, decreased appetite, inflammation of the gastrointestinal tract, or alopecia is reduced by at least about 5%, 10%, 20%, 30%, 40%, 50%, 60%, 70%, 80%, 90%, 95%, 98%, or 99% in comparison with chemotherapy or radiation treatment in which the palm pollen or extract thereof is not administered. In some embodiments, the adverse side effect is substantially or completely eliminated.

A method for treating, preventing, or ameliorating stomatitis is provided. The method includes orally administering a composition that includes a prophylactically effective or therapeutically effective unit dose of palm pollen or an extract thereof to the individual, wherein at least one stomatitis condition, such as gingivitis, denture stomatitis, physical stomatitis, xerostomia-induced stomatitis, contact stomatitits, and/or trauma (e.g., inflammation) from oral surgery and/or tooth extraction is prevented, reduced, or eliminated. In some embodiments, at least one stomatitis condition, such as such as gingivitis, denture stomatitis, physical stomatitis, xerostomia-induced stomatitis, contact stomatitits, and/or trauma (e.g., inflammation) from oral surgery and/or tooth extraction is reduced by at least about 5%, 10%, 20%, 30%, 40%, 50%, 60%, 70%, 80%, 90%, 95%, 98%, or 99%. In some embodiments, stomatitis is substantially or completely eliminated. In some embodiments, palm pollen is administered in conjunction with one or more additional agents for treatment, prevention, or amelioration of stomatitis. Non-limiting examples of such agents include antibiotics and antihistamines. The additional agent(s) may be administered simultaneously or sequentially with respect to administration of palm pollen. The effects of the additional agent(s) may be additive or synergistic with the effects of palm pollen.

A method for providing supplemental nutrition to an individual in need thereof is provided. For example, supplemental nutrition may be provided to an individual undergoing chemotherapy or radiation treatment for cancer or any individual for which such supplementation would be beneficial, such as an individual with a disorder or disease condition that requires supplemental nutrition, including, but not limited to, an individual with an inflammatory bowel disease (e.g., Crohn's disease, ulcerative colitis, irritable bowel syndrome) and/or an individual in need of hormone (e.g., estrogen) supplementation or replacement. The method includes orally administering a composition that includes a unit dose of palm pollen or an extract thereof to the individual, wherein at least one beneficial effect resulting from such administration is provided to the individual, such as improved energy, decreased fatigue, and improved appetite. The supplemental nutrition provided by palm pollen or an extract thereof may include, but is not limited to, natural lipids, rutin, triterpenoids, and carotenoids. In some embodiments, palm pollen or an extract thereof is administered to an individual in a method for hormone replacement, for example, a female individual in need of estrogen supplementation or replacement. For example, the method includes orally administering a composition that includes a unit dose of palm pollen or an extract thereof to the individual, wherein at least one estrogen (e.g., estrone, estradiol, estriol) is provided by the palm pollen or extract thereof to supplement or replace diminished estrogen levels in the individual.

In various embodiments of methods herein for oral administration of palm pollen, a powder, effervescent powder, tablet, effervescent powder, capsule, spray (e.g., aerosol), suspension, lozenge, mouthwash, or toothpaste that contains palm pollen or an extract thereof is administered orally. In one embodiment, up to about 2 g of a powder formulation (e.g., containing up to about 2 g of palm pollen or an equivalent amount of an extract thereof) is orally administered per day. In another embodiment, up to about 4 g of an effervescent powder (e.g., containing up to about 2 g of palm pollen or an equivalent amount of an extract thereof) is orally administered per day. In another embodiment, up to about 2 g of palm pollen or an equivalent amount of extract thereof is orally administered per day in a tablet or effervescent tablet formulation. In one example, 2 tablets are administered per day, each containing about 1 g of palm pollen or an equivalent amount of extract thereof. In another embodiment, up to about 2 g of palm pollen or an equivalent amount of extract thereof is orally administered in a capsule formulation. In one example, 2 capsules are administered per day, each containing about 1 g of palm pollen or an equivalent amount of extract thereof. In another embodiment, up to about 0.1 g of palm pollen or an equivalent amount of extract thereof is orally administered in a spray (e.g., aerosol) formulation. In one example, 2 sprays (e.g., aerosol sprays) are administered per day (e.g., sprayed onto an affected area in the oral cavity), each containing about 0.05 g of palm pollen or an equivalent amount of extract thereof. Powder, effervescent powder, or effervescent tablet formulations may be suspended in water or other suitable liquid for oral administration. In one example, about 2 g of powder formulation (e.g., about ½ teaspoon) is suspended in about ½ cup water and administered as a swish and swallow suspension.

A method for preventing alopecia (e.g., alopecia resulting from chemotherapy or radiation treatment for cancer) is provided. The method includes topically administering a composition that includes a prophylactically effective unit dose of palm pollen or an extract thereof to the scalp of the individual, wherein alopecia is partially, substantially, completely, or completely prevented. The administration may commence prior to, concurrent with the start of, or after the start of chemotherapy or radiation treatment. The administration may continue concurrently with the entire course of chemotherapy or radiation treatment or with a portion of the course of chemotherapy or radiation treatment, either continuously or intermittently during the course of treatment, and/or may continue after the course of chemotherapy or radiation treatment has concluded. In various embodiments, a spray (e.g., aerosol) or suspension that contains palm pollen or an extract thereof is administered topically to the scalp. Topical administration of palm pollen or an extract thereof may be used as the sole treatment for prevention of alopecia or may be used in combination with oral administration as described above.

In one embodiment, up to about 0.1 g of palm pollen or an equivalent amount of extract thereof is topically administered (e.g., topically administered to the scalp of an individual) in a spray (e.g., aerosol) formulation. In one example, 2 sprays (e.g., aerosol sprays) are administered per day (e.g., sprayed onto the scalp), each containing about 0.05 g of palm pollen or an equivalent amount of extract thereof. In another embodiment, up to about 0.2 g of palm pollen or an equivalent amount of extract thereof is topically administered (e.g., topically administered to the scalp of an individual) in a suspension formulation.

In some embodiments of any of the methods described herein, the palm pollen or extract thereof that is administered is from *Phoenix dactylefera* L.

Any of the methods described herein may be applied to human or veterinary (e.g., canine, feline) subjects. For veterinary applications, dosages may be adjusted dependent on the weight and species of the subject to be treated, which is within the skill in the art.

Methods of Preparation

Methods for preparing any of the DPP and/or DPP extract containing compositions described herein are provided. The methods include combining pollen from a palm species of the genus *Phoenix*, or an extract thereof, with at least one additional constituent (component) to facilitate oral or topical administration. In one embodiment, the method includes combining pollen or an extract thereof from *Phoenix dactylefera* L.

In one exemplary embodiment, preparation of the formulation includes the following steps: (1) mixing of non-DPP components, e.g., at a temperature less than about 50° C., or at a temperature lower than a temperature at which one or more protein(s) in DPP are denatured, or in circumstances in which an oleaginous phase is formed (for example, in an anhydrous formulation), the oleaginous phase may be melted at a temperature below about 60° C.; (2) addition of DPP or an extract thereof, e.g., at a temperature less than about 50° C., or at a temperature lower than a temperature at which one or more protein(s) in DPP are denatured; mixing and (3) mixing and homogenizing the formulation. It is desirable to avoid introduction of air, or to avoid introducing an amount of air that will oxidize and/or reduce activity of DPP, during the mixing and homogenization.

In one embodiment, the method includes combining DPP and one or more flow regulating agent(s) (e.g., silica (e.g., colloidal silica), silica gel, magnesium trisilicate, cornstarch, and/or talc) in a ratio to provide a powder formulation. Optionally, one or more flavoring agent(s) may also be added.

In another embodiment, the method includes combining DPP, compound(s) that provide an effervescent reaction (e.g., tartaric acid, citric acid, sodium bicarbonate), and one or more diluent(s) (e.g., spray dried lactose and/or starch) in a ratio to provide an effervescent powder. Optionally, one or more flavoring agent(s) may also be added.

In another embodiment, the method includes combining DPP, one or more diluent(s) (e.g., spray dried lactose and/or starch), and one or more anti-adhesive(s) (e.g., magnesium stearate, talc, and/or stearic acid) in a ratio to provide a tablet formulation.

In another embodiment, the method includes combining DPP, one or more diluent(s) (e.g., spray dried lactose and/or starch), one or more flow regulating agent(s) (e.g., silica (e.g., colloidal silica), silica gel, magnesium trisilicate, cornstarch, and/or talc), compound(s) that provide an effervescent reaction (e.g., tartaric acid, citric acid, sodium bicarbonate), one or more anti-adhesive(s) (e.g., magnesium stearate, talc, and/or stearic acid) in a ratio to provide an effervescent tablet formulation. Optionally, one or more flavoring agent(s) may also be added.

In another embodiment, the method includes combining DPP, one or more diluent(s) (e.g., spray dried lactose and/or starch), and one or more flow regulating agent(s) (e.g., silica (e.g., colloidal silica), silica gel, magnesium trisilicate, cornstarch, and/or talc) in a ratio to provide a formulation suitable for inclusion in a capsule, such as a hard gelatin capsule.

In another embodiment, the method includes combining DPP and one or more propellant (e.g., dichlorodifluoromethane (Propellant 12)) in a ratio to provide a formulation that may be packed under pressure to provide a metered pressurized dose of DPP (e.g., an aerosol formulation).

In another embodiment, the method includes combining DPP and one or more vehicle or carrier (e.g., polyethylene glycol (PEG) 400) in a ratio to provide a suspension suitable for topical administration. Optionally, one or more fragrance(s) may also be added.

Kits

Kits are provided for use in the methods described herein. The kits include a composition as described herein, for example including one or more unit dose of palm pollen or an extract thereof. Optionally, instructions for use and/or administration, e.g., oral or topical administration, of the composition, in a method described herein, are provided. Instructions may be provided in printed form or in the form of an electronic medium such as a CD or DVD, or in the form of a website address where such instructions may be obtained or a mobile application.

Suitable packaging is provided. As used herein, "packaging" refers to a solid matrix or material customarily used in a system and capable of holding within fixed limits a composition suitable for administration to an individual as described herein. Such materials include glass and plastic (e.g., polyethylene, polypropylene, and polycarbonate) bottles, sachets, containers that provide pressurized metered doses of an aerosol formulation, vials, paper, plastic, and plastic-foil laminated envelopes and the like. If e-beam sterilization techniques are employed, the packaging should have sufficiently low density to permit sterilization of the contents.

Kits may also optionally include equipment and/or dispensers for oral or topical administration of a palm pollen formulation as described herein.

The following example is intended to illustrate, but not limit, the invention.

EXAMPLES

Example 1

A study was undertaken to evaluate the effectiveness of DPP in the prevention and treatment of oral mucositis induced by radiation and chemotherapy in patients with head and neck cancers.

Study Design

Twenty human patients with head and neck cancers were enrolled in the study prior to initiation of first line chemotherapy and/or radiation treatment. Ten subjects were treated with DPP administered orally (2 g daily for 30 days) as a swish and swallow suspension, and ten control subjects received the facility standard of care for oral mucositis. The characteristics of subjects in the DPP treated and control groups are shown in Table 2.

TABLE 2

Subject characteristics within DPP treated group and control group

| Subject | DPP treated (n = 10) | Control (n = 10) |
| --- | --- | --- |
| Male | 5 | 6 |
| Female | 5 | 4 |
| Median Age | 43.5 | 47.5 |
| Smoker | 3 | 3 |
| Non-smoker | 7 | 7 |
| Average Body Weight (kg) | 76.3 | 74.1 |
| Tumor Type | Squamous cell carcinoma (8) Adenocarcinoma (1) Hodgkin's Lymphoma (1) | Squamous cell carcinoma (10) |
| Cancer Treatment | Chemotherapy* and radiation (8) Radiation only (2) | Chemotherapy* and radiation (10) |

*Chemotherapy treatment of Cisplatin 100 mg/m$^2$ every 3 weeks for 3 cycles
**Radiation treatment of 3D conformal radiotherapy 50 Gy to 72 Gy in 200 cGy conventional fractionation DPP treatment was self-administered, nightly for 42 days, starting one day prior to initiation of chemotherapy or radiation treatment. DPP was formulated for oral administration and supplied as a powder (99.5% DPP; 0.5% colloidal silica) to be mixed in water by the study subject as follows: 2 grams of DPP powder formulation (½ teaspoon) added to ½ cup (125 ml) water. The subjects were instructed to prepare the suspension just prior to use and to administer it once a day at bedtime, swishing portions of the suspension through the mouth for approximately 15-20 seconds and swallowing until the entire ½ cup suspension was consumed. Subjects were instructed to follow standard oral hygiene prior to dosing.

Objective oral assessments using the Oral Mucositis Assessment Scale (OMAS) and digital photography of the oral cavity were conducted as baseline and every two weeks thereafter while the subjects received the treatment. Study subjects evaluated the treatment impact by visual analog scales (VAS) for severity of mouth pain and ability to swallow. Examples of OMAS and VAS evaluation procedures are provided in Sonis (2004) *Journal of Supportive Oncology* 2:3-8).

Results

A significant reduction in the incidence and severity of oral mucositis was observed in the DPP treatment group in comparison to the control group, as shown in Tables 3-5. Table 3 shows that DPP administration before treatment almost prevented mucositis. The reduction in OMAS in the DPP treated group was statistically significant during the evaluation period. Similarly, the pain intensity level was significantly reduced in comparison with the control group (Table 4).

During the treatment period, 80% of the patients in the control group needed to change their diet to soft or liquid food (WHO Grade ⅔ mucositis), while only one patient (10%) of the DPP group required soft food (Grade 2).

Visually, erythema of mucosa, edema, and severe ulcers that were observed in the control arm were absent in the DPP treated group. Table 5 shows the impact of the treatment on the ability to swallow in the DPP treated and control groups.

TABLE 3

Mean OMAS in DPP treated group vs. control group

| Evaluation Period | Mean OMAS ± Standard Deviation | | Significance |
|---|---|---|---|
| | DPP treated (n = 10) | Control (n = 10) | |
| Day 1 | 0.7 ± 0.57 | 1.70 ± 1.66 | Not significant |
| Day 15 | 0.2 ± 0.30 | 7.6 ± 2.26 | Significant |
| Day 29 | 0 ± 0.0 | 7.0 ± 2.80 | Significant |

Confidence level 95%

TABLE 4

Mean oral pain level in DPP treated group vs. control group

| Evaluation Period | Mean Oral Pain Level ± Standard Deviation | | Significance |
|---|---|---|---|
| | DPP treated (n = 10) | Control (n = 10) | |
| Day 1 | 0.7 ± 1.30 | 1.5 ± 1.11 | Not significant |
| Day 15 | 0.07 ± 0.70 | 2.8 ± 0.80 | Significant |
| Day 29 | 0 ± 0.0 | 3.0 ± 0.81 | Significant |

Confidence level 95%

TABLE 5

Mean impact on swallowing in DPP treated group vs. control group

| Evaluation Period | Mean Impact on Swallowing ± Standard Deviation | | Significance |
|---|---|---|---|
| | DPP treated (n = 10) | Control (n = 10) | |
| Day 1 | 0.320 ± 0.305 | 0.07 ± 0.07 | Not significant |
| Day 15 | 0.120 ± 0.275 | 2.9 ± 2.35 | Significant |
| Day 29 | 0 ± 0.0 | 4.1 ± 2.11 | Significant |

Confidence level 95%

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated in the appended claims.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A method for treating, preventing, or ameliorating at least one adverse side effect of chemotherapy or radiation treatment for cancer in an individual in need thereof, said method comprising administering an effective amount of a composition comprising a unit dose of pollen from a palm species of the genus *Phoenix* or an extract thereof to the individual,
wherein the individual is a human, and
wherein the at least one adverse side effect comprises mucositis, stomatitis, nausea, vomiting, decreased appetite, inflammation of the gastrointestinal tract, or alopecia.

2. A method according to claim 1, wherein said unit dose is about 0.05 g to about 6 g of palm pollen per day.

3. A method according to claim 1, wherein said unit dose is formulated as a powder, a tablet, a capsule, an aerosol, a suspension, or an effervescent powder or tablet.

4. A method according to claim 1, wherein said palm pollen or extract thereof is date palm pollen or an extract thereof from *Phoenix dactylefera L.*

5. A method according to claim 1, wherein said administration commences prior to initiation of chemotherapy or radiation treatment.

6. A method according to claim 1, comprising orally administering about 2 g per day of said palm pollen in a liquid suspension, wherein said administration prevents, treats, or ameliorates oral mucositis.

7. A method according to claim 1, comprising orally administering up to about 2 g of said palm pollen in a powder, effervescent powder, tablet, effervescent tablet, or capsule formulation per day, wherein said administration prevents, treats, and/or ameliorates mucositis, stomatitis, nausea, vomiting, decreased appetite, inflammation of the gastrointestinal tract, and/or alopecia.

8. A method according to claim 1, comprising orally administering about 0.1 g of said palm pollen in an aerosol formulation per day, wherein said administration is directed to areas of inflammation in the oral cavity of the individual, and wherein said administration treats and/or ameliorates oral mucositis and/or stomatitis.

* * * * *